United States Patent
Epstein et al.

(10) Patent No.: US 7,081,103 B2
(45) Date of Patent: *Jul. 25, 2006

(54) DIRECT DUAL FILLING DEVICE FOR SEALING AGENTS

(75) Inventors: Gordon Howard Epstein, Fremont, CA (US); Mitchell E. Levinson, Pleasanton, CA (US); Richard Spero, Brentwood, CA (US)

(73) Assignee: Baxter International Inc., Deerfield, IL (US)

( * ) Notice: Subject to any disclaimer, the term of this patent is extended or adjusted under 35 U.S.C. 154(b) by 172 days.

This patent is subject to a terminal disclaimer.

(21) Appl. No.: 10/287,934

(22) Filed: Nov. 4, 2002

(65) Prior Publication Data
US 2003/0083606 A1 May 1, 2003

Related U.S. Application Data

(63) Continuation of application No. 09/307,056, filed on May 7, 1999, now Pat. No. 6,475,183.

(60) Provisional application No. 60/087,856, filed on Jun. 3, 1998.

(51) Int. Cl.
*A61M 37/00* (2006.01)

(52) U.S. Cl. .................. 604/82; 606/214; 222/129; 604/518

(58) Field of Classification Search .......... 604/82–88, 604/92, 139, 181, 187, 200, 201, 205, 218, 604/232, 235, 244, 403, 407, 410–416, 191; 222/80–83, 83.5, 89, 135, 129; 206/222; 215/247, 355, DIG. 8, DIG. 3, 249, 250, 215/253; 606/93, 214
See application file for complete search history.

(56) References Cited

U.S. PATENT DOCUMENTS

| 766,202 A | | 8/1904 | Vandewater |
| 1,740,717 A | * | 12/1929 | Waite .................. 215/247 |
| 2,122,722 A | | 7/1938 | O'Neil |
| 2,135,386 A | * | 11/1938 | Crabbe .................. 215/247 |
| 2,734,649 A | * | 2/1956 | Callahan et al. ........... 215/233 |
| 2,783,908 A | * | 3/1957 | Winfield ................. 215/247 |
| 2,906,423 A | * | 9/1959 | Sandhage ................. 215/249 |
| 3,134,407 A | | 5/1964 | Wegman |
| 3,136,440 A | * | 6/1964 | Krug et al. ............... 215/247 |
| 3,405,706 A | | 10/1968 | Cinqualbre |
| 3,767,085 A | | 10/1973 | Cannon |
| 3,774,654 A | | 11/1973 | Hjermstad |

(Continued)

FOREIGN PATENT DOCUMENTS

EP 0156098 A2 12/1984

(Continued)

*Primary Examiner*—Niccholas Lucchesi
*Assistant Examiner*—Theodore J. Stigell
(74) *Attorney, Agent, or Firm*—Jeffrey C. Nichols; Bradford R. L. Price; Austin J. Foley

(57) ABSTRACT

A filling device for connecting a dispensing instrument having multiple fluid reservoirs to multiple containers is disclosed. More particularly, the present invention discloses a connecting device capable of coupling the individual reservoirs of a dispensing instrument to multiple fluid containers. The apparatus includes a body, a collar extending from the body, a plurality of tubes in fluid communication with a plurality of inlet ports formed in the body, and a hood adapted to simultaneously receive a plurality of containers therein. The containers are positioned within the hood to allow the plurality of tubes to simultaneously and separately draw fluid from the fluid containers and transferring the material into the individual reservoirs of the dispensing instrument.

11 Claims, 12 Drawing Sheets

U.S. PATENT DOCUMENTS

| | | | |
|---|---|---|---|
| 3,776,700 A | 12/1973 | Gallant | |
| 3,807,467 A | 4/1974 | Tascher et al. | |
| 3,833,030 A | 9/1974 | Waldbauer, Jr. et al. | |
| 4,128,098 A | 12/1978 | Bloom et al. | |
| 4,325,913 A | 4/1982 | Wardlaw | |
| 4,359,049 A | 11/1982 | Redl et al. | |
| 4,434,820 A | 3/1984 | Glass | |
| 4,552,277 A | 11/1985 | Richardson et al. | |
| 4,629,455 A | 12/1986 | Kanno | |
| 4,631,055 A | 12/1986 | Redl et al. | |
| 4,690,165 A | 9/1987 | Leytes et al. | |
| 4,810,123 A | 3/1989 | Bruggeman | |
| 4,846,405 A | 7/1989 | Zimmermann | |
| 4,856,567 A | 8/1989 | Cosmai | |
| 4,883,483 A | 11/1989 | Lindmayer | |
| 4,902,281 A | 2/1990 | Avoy | |
| 4,969,669 A | 11/1990 | Sauer | |
| 4,978,336 A | 12/1990 | Capozzi et al. | |
| 5,116,315 A | 5/1992 | Capozzi et al. | |
| 5,163,433 A | 11/1992 | Kagawa et al. | |
| 5,171,146 A | 12/1992 | Guerci | |
| 5,195,985 A | 3/1993 | Hall | |
| 5,226,877 A | 7/1993 | Epstein | |
| 5,240,146 A | 8/1993 | Smedley et al. | |
| 5,247,972 A | 9/1993 | Tetreault | |
| 5,297,561 A | 3/1994 | Hulon | |
| 5,329,976 A | 7/1994 | Haber et al. | |
| 5,368,563 A | 11/1994 | Lonneman et al. | |
| 5,445,631 A | 8/1995 | Uchida | |
| 5,478,323 A | 12/1995 | Westwood et al. | |
| 5,487,738 A * | 1/1996 | Sciulli | 604/414 |
| 5,542,760 A | 8/1996 | Chanoch et al. | |
| 5,554,128 A | 9/1996 | Hedges | |
| 5,582,596 A | 12/1996 | Fukunaga et al. | |
| 5,585,007 A | 12/1996 | Antanavich et al. | |
| 5,591,143 A | 1/1997 | Trombley, III et al. | |
| 5,605,255 A | 2/1997 | Reidel et al. | |
| 5,605,541 A | 2/1997 | Holm | |
| 5,612,050 A | 3/1997 | Rowe et al. | |
| 5,656,035 A * | 8/1997 | Avoy | 604/191 |
| 5,665,067 A | 9/1997 | Linder et al. | |
| 5,759,169 A | 6/1998 | Marx | |
| 5,759,171 A | 6/1998 | Coelho et al. | |
| 5,788,662 A | 8/1998 | Antanavich et al. | |
| 5,827,262 A | 10/1998 | Neftel et al. | |
| 5,894,870 A | 4/1999 | Maxwell | |
| 5,901,883 A | 5/1999 | Ritsche | |
| 5,935,437 A | 8/1999 | Whitmore | |
| 5,971,956 A | 10/1999 | Epstein | |
| 5,989,215 A | 11/1999 | Delmotte et al. | |
| 6,063,297 A | 5/2000 | Antanavich et al. | |
| 6,475,183 B1 * | 11/2002 | Epstein et al. | 604/82 |
| 6,488,650 B1 * | 12/2002 | Epstein et al. | 604/82 |

FOREIGN PATENT DOCUMENTS

| | | |
|---|---|---|
| EP | 0302411 B1 | 6/1992 |
| EP | 0738498 A1 | 10/1996 |
| EP | 0156098 B1 | 11/1998 |
| WO | WO 8904676 | 6/1989 |
| WO | WO 9001959 | 3/1990 |
| WO | WO 9406487 | 3/1994 |
| WO | WO 9629113 A1 | 9/1996 |
| WO | WO 9725015 | 7/1997 |
| WO | WO 9728834 A1 | 8/1997 |
| WO | WO 9807846 A1 | 2/1998 |
| WO | WO 9846300 A1 | 10/1998 |
| WO | WO 99/17833 * | 4/1999 |
| WO | WO 99/17833 A * | 4/1999 |
| WO | WO 9917833 A * | 4/1999 |
| WO | WO 9917833 A1 | 4/1999 |
| WO | WO 9930769 | 6/1999 |
| WO | WO 9932155 | 7/1999 |
| WO | WO 9939642 A1 | 8/1999 |
| WO | WO 9962588 A1 | 12/1999 |

* cited by examiner

DIRECT DUAL FILLING DEVICE FOR SEALING AGENTS

CROSS REFERENCE TO A RELATED APPLICATION

This is a continuation of application Ser. No. 09/307,056, filed May 7, 1999 now U.S. Pat. No. 6,475,183 and entitled "DIRECT DUAL FILLING DEVICE FOR SEALING AGENTS", the disclosure of which is hereby incorporated herein by reference thereto. This application is a continuation of U.S. provisional application 60/087,856 filed on Jun. 3, 1998 to Epstein, the subject matter of which is hereby incorporated by reference. This application discloses subject matter related to our U.S. application Ser. No. 08/838,078, now issued U.S. Pat. No. 6,331,172, and Ser. No. 08/839,614, now issued U.S. Pat. No. 5,971,956, both filed Apr. 14, 1997, to patent application Ser. No. 08/946,364 filed Oct. 7, 1997, now issued U.S. Pat. No. 6,007,515, and to patent application Ser. No. 09/037,160 filed Mar 9, 1998, now issued U.S. Pat. No. 6,063,055, all naming Gordon H. Epstein as first inventor. The disclosures of the aforementioned U.S. patent applications, "the above applications" are hereby incorporated herein by reference thereto.

BACKGROUND OF THE INVENTION

1. Field of the Invention

The present invention relates to a filling device for an applicator which applies multiple fluid sealant components to a work surface and is particularly, although not exclusively, useful for applying tissue sealant components to biological tissue to effect hemostasis or achieve other therapeutic results. More particularly, it relates to a dual compartment enclosed direct filling device for a hand-held applicator.

2. Description of Related Art Including Information Disclosed Under 37 CFR 1.97 and 37 CFR 1.98

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first component containing fibrinogen and Factor XIII and on the other hand a second component which usually includes thrombin, and calcium ions. The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging. These problems must be overcome in devising suitable applicators, methods of application and devices suitable for filling said applicators.

A popular manually operable applicator for such two-component sealants employs a dual syringe construction wherein two syringes, connected by a yoke, each provide a reservoir for one of the components. In most prior devices, the sealant components are discharged in separate streams and mixed externally of the applicator. Such applicators are similar in principle to household epoxy glue applicators commonly available in hardware stores.

Until May of 1998, when the FDA first approved such products, fibrin sealant was not commercially available in the US, therefore use of fibrin sealant was limited to supplies produced within the clinic, which are not subject to FDA control.

As taught in Epstein U.S. Pat. No. 5,266,877 and in our assignee's international application PCT/US98/07846, components of the sealant can be placed in separate compartments in a flat filler tray for transfer to an applicator. Though useful as a device to permit rapid and reliable filling of a dual syringe applicator at the point of use, such filler trays are not suitable for external storage of the sealant components. This process can be time consuming and it requires a significant degree of care to efficiently transfer the sealant to the applicator. Also, a small amount of sealant will be left in the tray, and it is thus wasted. Furthermore the transfer of sealant components to multiple storage containers raises the likelihood in which the sealants will gather bio-burden, and bacteria, which can threaten the sterility of the sealant.

After FDA approval, however, fibrin sealant is now commercially available in the US. This availability has created a need for an effective and efficient device useful for transferring the components of the sealant, from commercially available or standardized, bottle-like storage containers, into an applicator.

There is accordingly a need for a device which can effectively deliver, in a sterile environmet, multiple sealant components directly from their storage containers to an applicator.

SUMMARY OF THE INVENTION

The present invention solves the problem of effectively delivering multiple sealant components directly from commercially available or standardized storage containers, for example, bottles, to an applicator while allowing the use of the entire fill device within a sterile field.

In one aspect, the invention provides a direct dual filling device for the multiple sealant components of a liquid sealant, at least two of said components being complementary one to the other and polymerize when mixed, the direct filling device comprising a body having a plurality of inlet ports connected to drawing tubes which pierce the protective covering of commercially available bottles, the bottles containing the sealant components. The device also having a hood which snaps onto a base thereby enclosing the bottles within the structure, allowing the device to be brought into a sterile field. The base having slanted bottle supports which hold the bottles in a tilted position. This feature allows the drawing tubes to extract virtually all of the fluid contained within the bottles. The device can be attached to an applicator with keying such that when the plunger of the applicator is retracted, fluid is drawn from each respective bottle to the proper reservoir contained within the applicator.

The invention enables multiple sealant components to be directly delivered from their commercially available containers into an applicator without significant risk of contamination of the sealant components, and with minimal wasting of the sealant components. The different sealant components are delivered directly from their containers into separate individual reservoirs, thereby preventing coagulation of the sealant components. Once the hood of the device is guided onto the bottles and snapped onto the base, the entire device can be brought into the sterile environment.

BRIEF DESCRIPTION OF THE DRAWINGS

One way of carrying out the invention is described in detail below with reference to the drawings which illustrate one or more specific embodiments of the invention and in which.

DESCRIPTION OF THE PREFERRED EMBODIMENTS

Figure 1:
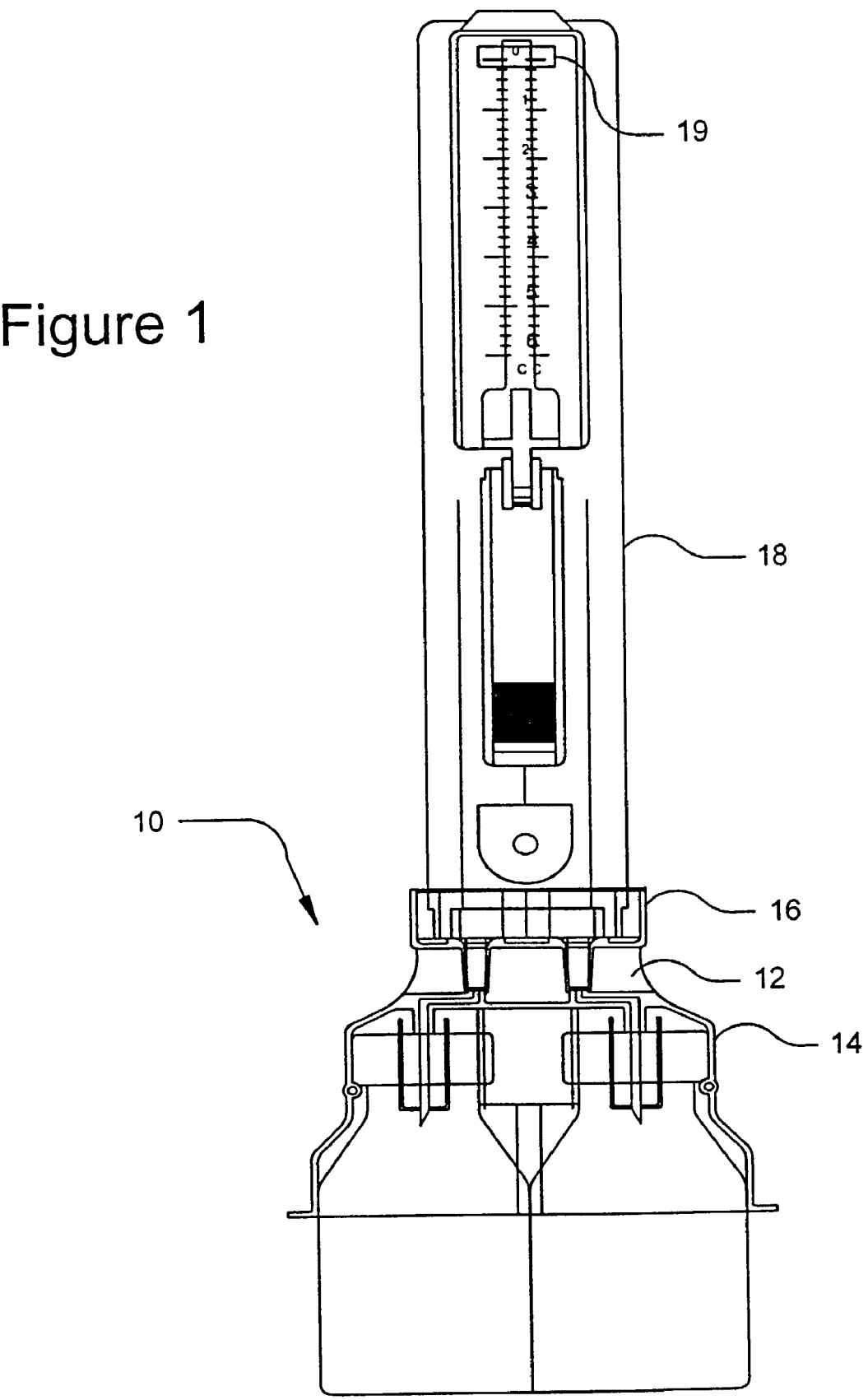
FIG. 1 is a side elevational view of a direct dual filling device connected to an applicator according to the present invention.
Figure 2:
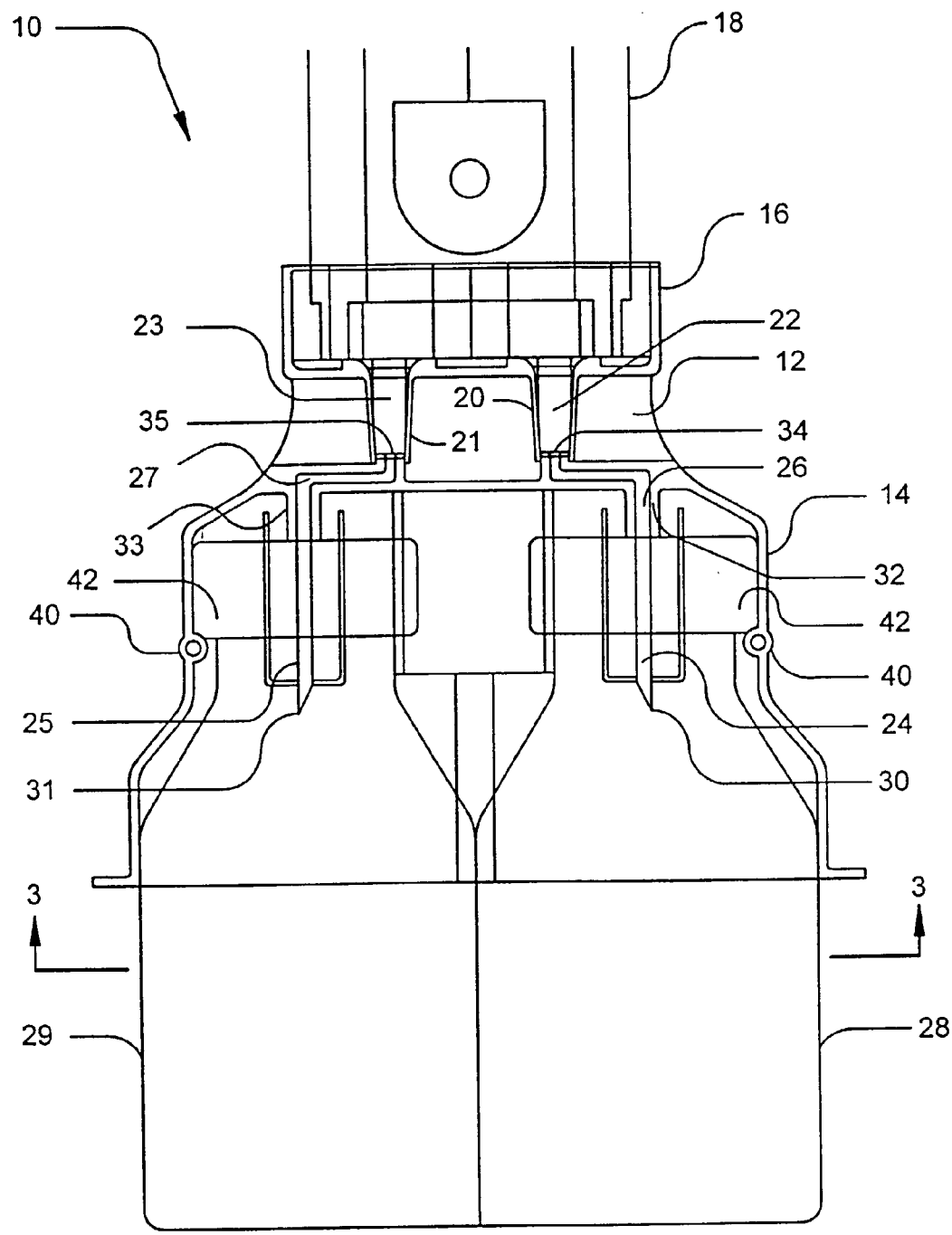
FIG. 2 is an enlarged side elevational view of the present invention.

Referring to FIGS. 1 and 2 of the drawings, the direct dual filling device 10 comprises a body 12, a hood 14 and a collar 16 which is adapted to fit an applicator 18. The inventive device is preferably constructed out of a clear thermoplastic material such as polycarbonate, polystyrene, polypropylene, polytetrafluoroethylene, acrylonitrile butadiene-styrene or acrylic, however any suitable material may be used.

Applicator 18 preferably has at least two fluid reservoirs for separately holding and controllably dispensing reactable fluids, each of the fluid reservoirs being connected to a syringe by a fluid conduit. The applicator is of the type primarily used for applying multiple fluid sealant components to biological tissue to effect hemostasis or achieve other therapeutic results. However the inventive filling device can be adapted to fit applicators having a wide variety of uses which require the direct filling of fluids into separate reservoirs located within an applicator.

Located within body 12 are inlet ports 20 and 21 which are adapted to receive syringes 22 and 23 of applicator 18. Rubber O-rings 34 and 35 are positioned within inlet ports 20 and 21 respectively, such that an air tight seal is formed.

Inlet ports 20 and 21 are connected to drawing tubes 24 and 25 by transverse channels 26 and 27 respectively, which drawing tubes 24 and 25 extend into bottles 28 and 29.

Drawing tubes 24 and 25 should have sufficient length to extract substantially all the liquid contained within the bottle, or conversely they should have a length such that when the system is inverted substantially all of the liquid can be extracted. Drawing tubes 24 and 25 are preferably configured with pointed ends 30 and 31 which have the ability to pierce the protective packaging found on standard medical fluid bottles 28 and 29 and form a seal. Drawing tubes 24 and 25 are preferably formed out of a metallic material, however any suitable material such as thermoplastic may be used. The tubes can also have the ability to be removed from support sleeves 32 and 33 for replacement.

Channel 26 allows the fluid contained within right bottle 28 to be drawn through tube 24 and into syringe 22 for deposit within the proper receptacle located within applicator 18 without coming into contact with the fluid contained within bottle 29. Similarly, channel 27 allows the fluid contained within left bottle 29 to be drawn through tube 25 and into syringe 23 for deposit within the proper receptacle located within applicator 18 without coming into contact with the fluid contained within bottle 28. This allows the simultaneous filling of both sides of the applicator directly from the commercially available containers. Channels 26 and 27 can be formed out of thermoplastic tubing or molded directly into body 12 of the direct filling device 10.

Figure 3:
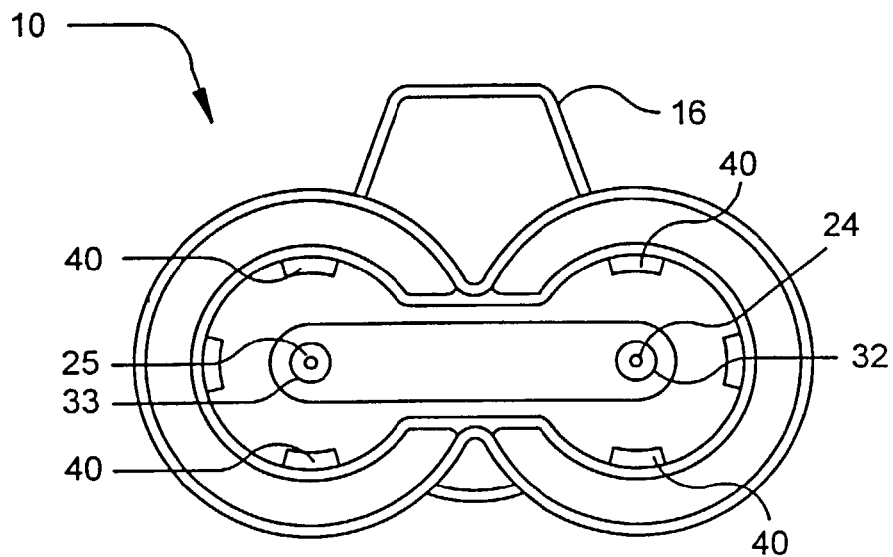
FIG. 3 is a view of the present invention along section lines 3—3 of FIG. 2.

In order to fill applicator 18 directly from bottles 28 and 29, hood 14 is placed over said bottles such that pointed tips 30 and 31 are approximately centered on the protective seal covering the bottles. The contoured shape of hood 14 guides the inventive device as the bottles are seated and snap into place within hood 14 by locking members 40. As clearly shown in FIG. 3, locking members 40 are located within hood 14 such that they move apart when cap 42 of its respective bottle passes by during the insertion of the bottle, then once the bottle has reached the proper location locking members 40 retract under bottle cap 42 to lock or "seat" the bottles in place. Once the bottles have been seated the system may be inverted to ensure that all of the fluid is draw out of the bottles.

The plunger 19 of applicator 18 is then retracted thereby drawing the fluid contained within bottles 28 and 29 through their respective drawing tubes and channels into the syringes of applicator 18 for deposit within a reservoir.

Figure 4:
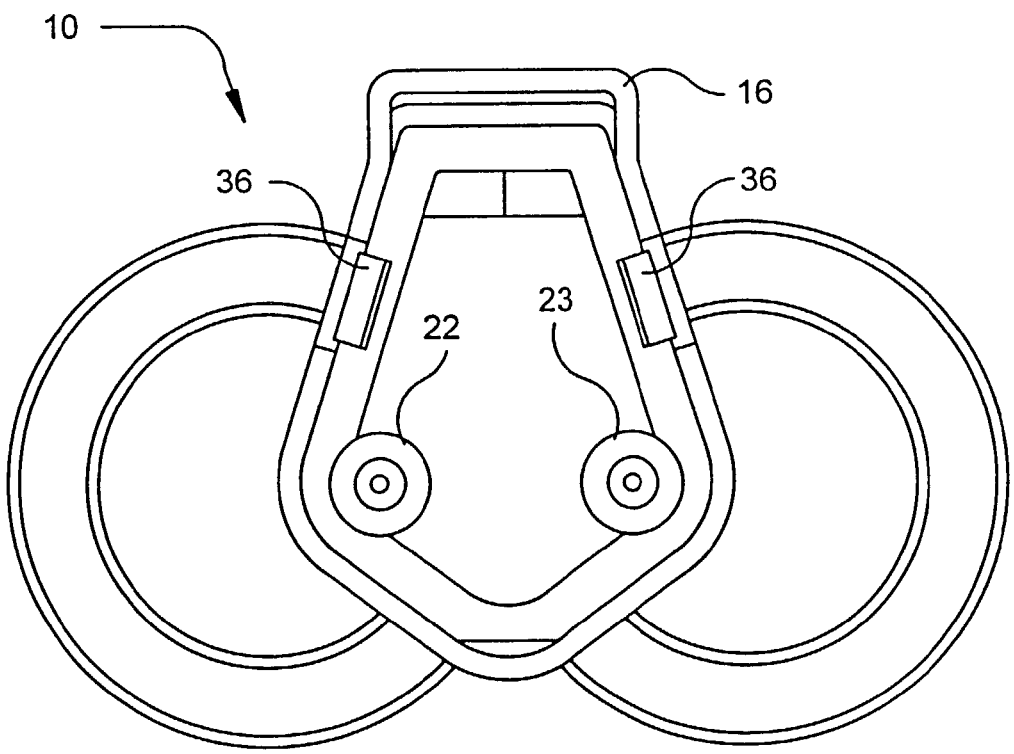
FIG. 4 is a top view of the present invention.

The direct filing device 10, as shown in FIG. 4, is connected to applicator 18 by a pair of snap fit members 36. Applicator 18 is placed over the filling device such that the syringes are approximately centered over inlet ports 22 and 23, then pressed down until locked in place by snap fit members 36. The novel shaping of the collar 16 allows filling device 10 to mate with applicator 18 in only one orientation, thereby "keying" the fill device to the applicator. The general pentagon shape precisely fits to the applicator body in the same manner as interchangeable applicator tips or heads, which are used for droplet or spray dispensing of sealant. This feature of keying the filling device collar to the applicator ensures the proper fibrin components are delivered to their respective reservoirs without significant risk of cross-contamination, particularly when refilling.

Figure 5:
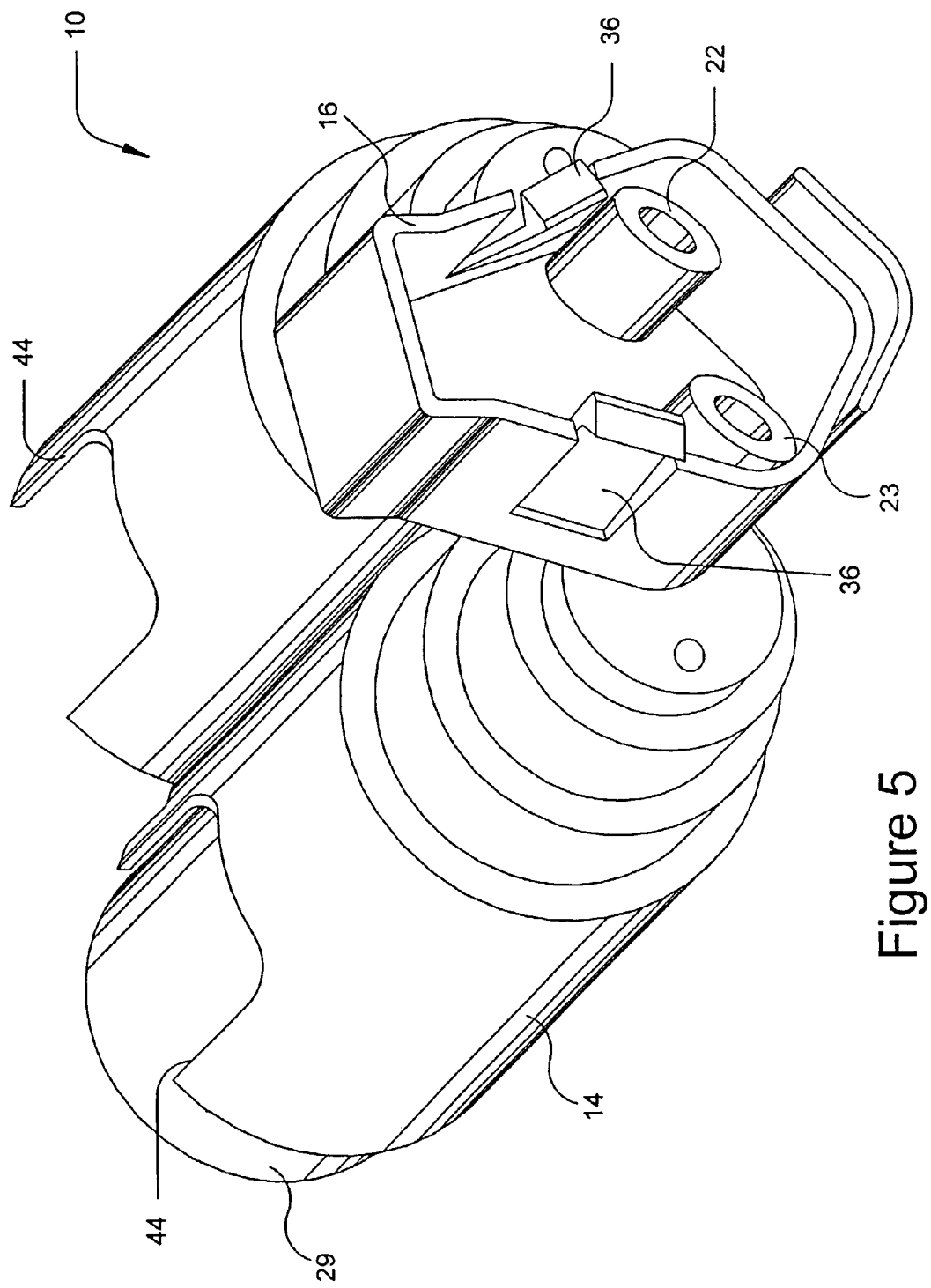
FIG. 5 is a perspective view of the present invention.

As depicted in FIG. 5, bottle 29 is inserted into hood 14 until seated by locking members 40. As can be clearly seen, hood 14 has a recess 44 which aides the user in removal of the bottles. Recess 44 is also useful, if hood 14 is opaque, to view any labels present on the bottle so it can be verified that the proper components are delivered into the proper reservoirs. Also shown is the contoured shape of hood 14. The shape can be varied to allow use of different types and shapes of bottles. The hood can also be modified so that each side allows insertion of a different shaped bottle, thereby keying the bottles to the fill device. This in conjunction with the novel shape of the collar is important in ensuring that the proper components are delivered to the proper reservoirs within the applicator.

The direct dual filling device embodiment shown in FIGS. 6–11 is a more detailed embodiment of the invention which includes most of the features shown in the embodiment of FIGS. 1–5 and is suitable for manufacturing from injected molded plastics components. As will be described, several of the parts of the direct dual filling device shown in FIGS. 6–11 embody similar construction and functionality to the components of the embodiment shown in FIGS. 1–5.

Figure 6:
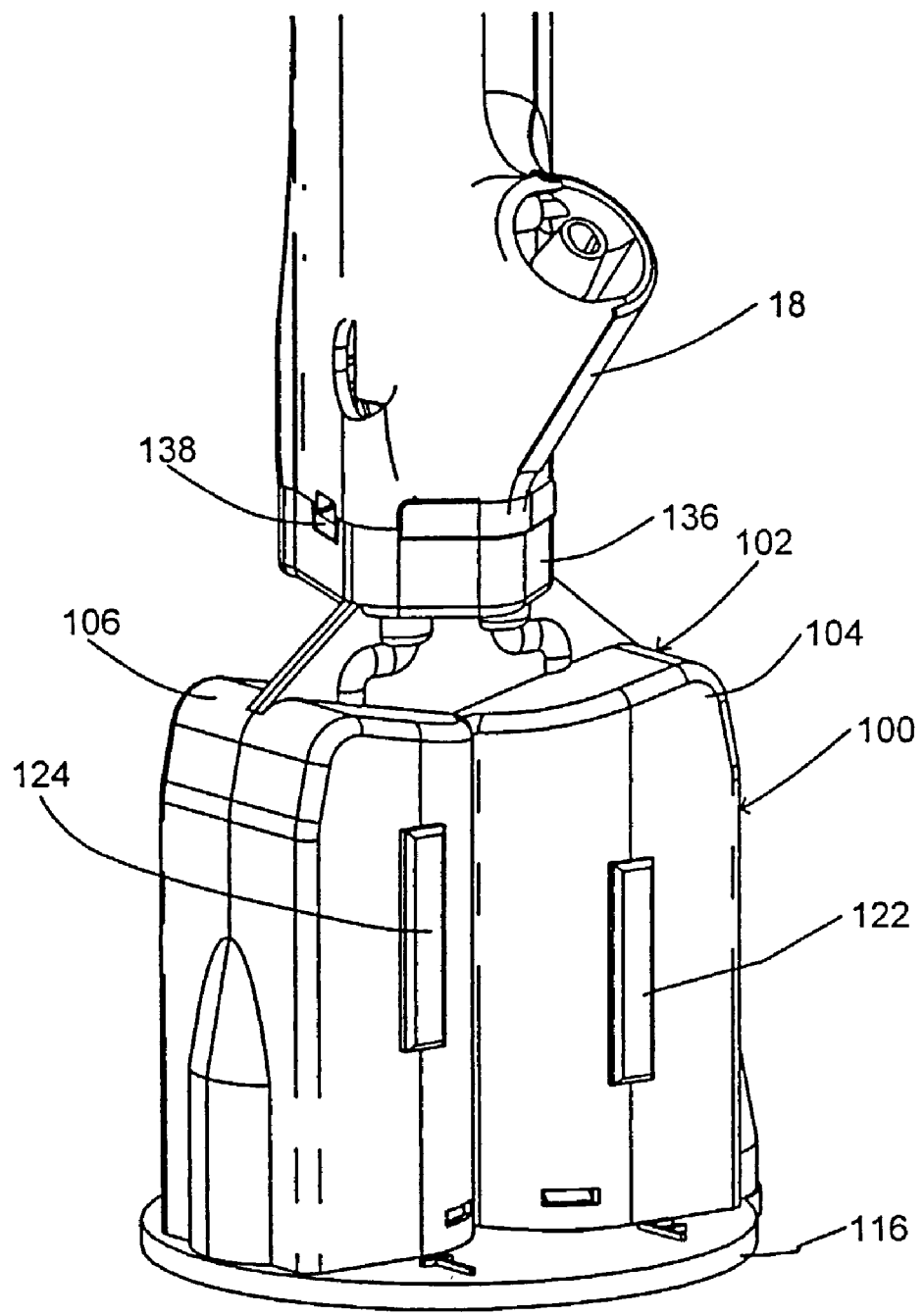
FIG. 6 is a perspective view of a direct dual filling device connected to an applicator according to an alternative embodiment of the present invention.
Figure 7:
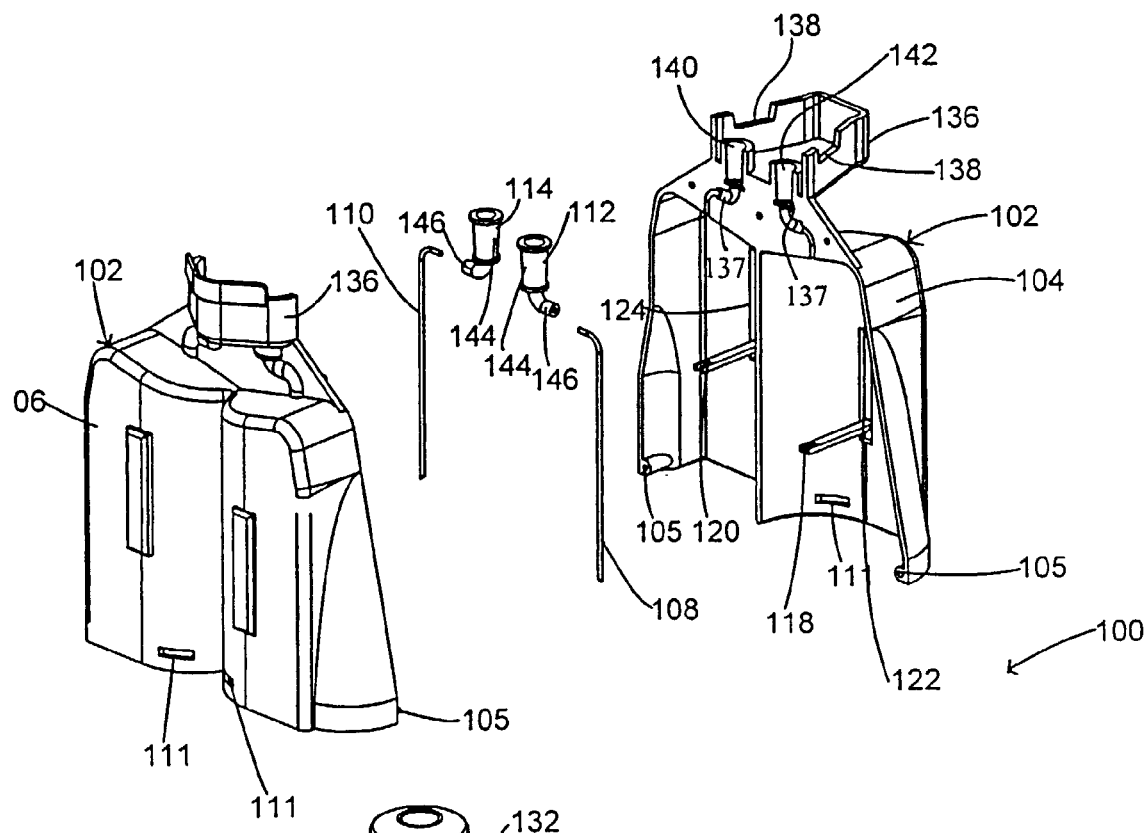
FIG. 7 is an exploded view of an alternative embodiment of the present invention.
Figure 7:
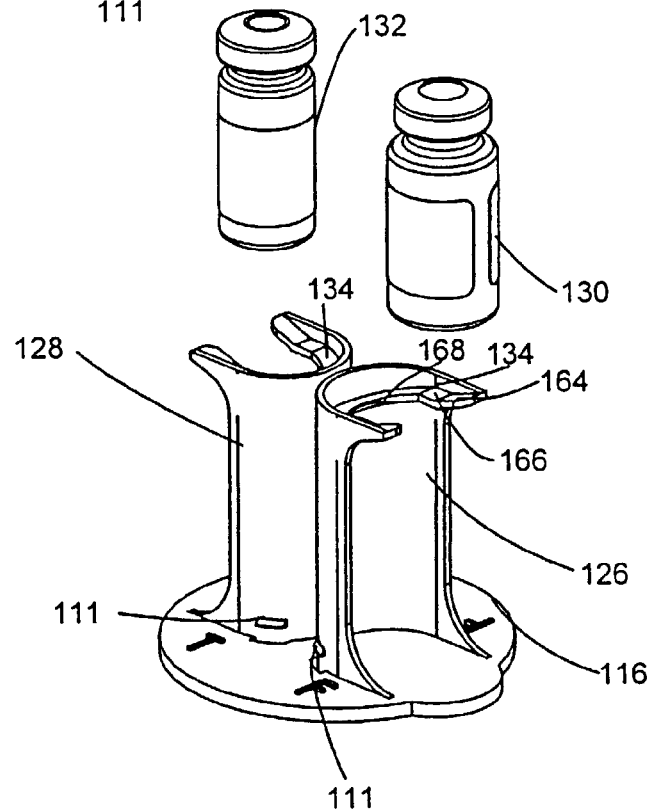

Many individual structural features of the components of the direct dual filling device can be seen from the exploded view of FIG. 7, while FIGS. 8–13 show additional structural features and relationships of the internal components and FIG. 6 shows the overall external appearance of the direct tool filling device while in use.

Referring to FIG. 7, the direct dual filling device 100, shown in exploded view, comprises a hood 102, having a first half 104 and a second half 106, a pair of drawing tubes 108 and 110, a pair of fluid conduits 112 and 114, and a base 116. First-half 104 and second half 102, of hood 102 have a pair of drawing tube guides 118 and 120, and a pair of recesses 122 and 124. Base 116 has a pair of vial supports 126 and 128 which are configured to support vials 130 and 132. Additionally, each of the vial supports 126 and 128 have a vial support surface 134.

Hood 102 can be contoured to resemble the shape of the filling device when assembled with agent vials. The shape can also vary to allow use of different types and shapes of bottles. The hood can be modified so that each side allows insertion of a different shaped bottle, thereby keying the bottles to the fill device. This in conjunction with the novel shape of the collar is important in ensuring that the proper components are delivered to the proper reservoirs within the applicator.

In preferred embodiments, hood 102 and base 116 are essentially rigid, injected molded components having limited resilience in their thinner sections. Hood 102 is also preferably formed from a clear plastic such as polycarbonate or SAN. In contrast, fluid conduits 112 and 114 are preferably fabricated from a distinctly elastomeric, resilient molding material such as silicone rubber.

Once assembled hood 102 is configured to snap into the base by use of snap fit members 111. Hood 102 and base 116 are configured such that they may only be assembled in one direction, so in use, the operator cannot assemble the device incorrectly. Base 116 and hood 102 are also color-coded to indicate which side is for the thrombin vial in which side is for the fibrinogen vial. Furthermore, base 116 is labeled with a "T" indicating the side for thrombin, and an "F" indicating the side for fibrinogen.

When assembled, the upper portions of first-half 104 and second half 106 combine to form a collar 136, embodying features of collar 16. A pair of channels 137 having inlet ports 140 and 142 are also defined within hood 102. Channels 137 are configured to retain fluid conduits 112 and 114.

Fluid conduits 112 and 114 comprise a cylindrical cup 144 and a tubular arm 146, which fits suitably within channel 137. Cups 144 are internally configured to be pressed into tight sealing engagement, when so mounted to syringes 22 and 23 of applicator 18, with the ends of sealant components syringes mounted in a mating applicator body, to receive liquid components therefrom. Tubular arms 146 of fluid conduits 112 and 114 are flexible and can readily be manipulated during assembling of filling device 102. The ends of tubular arms 146 are configured to be fitted with the ends of drawing tubes 108 and 110 respectively. This configuration allows liquid components to be drawn through tube 108 into fluid conduit 112 and stored within the respective reservoir located within applicator 18. Similarly, liquid component may be drawn through tube 110 into fluid conduit 114 and stored within the other reservoir located within applicator 18 without significant risk of contamination. When assembled, the filling device provides an airtight interface from the drawing tubes to the applicator reservoir.

Drawing tubes 108 and 110 should have sufficient length to extract substantially all the liquid contained within the corresponding vial. Drawing tubes 108 and 110 are preferably configured with a pointed end which has the ability to pierce the protective seal found on standard medical fluid bottles thereby forming a seal. Drawing tubes 108 and 110 generally resemble a needle, and are preferably formed out of a metallic material, however any suitable material such as thermoplastic may be used. Both of the tubes may be of similar diameter, however the tube diameter may differ to accommodate liquids having differing viscosities.

Figure 13:
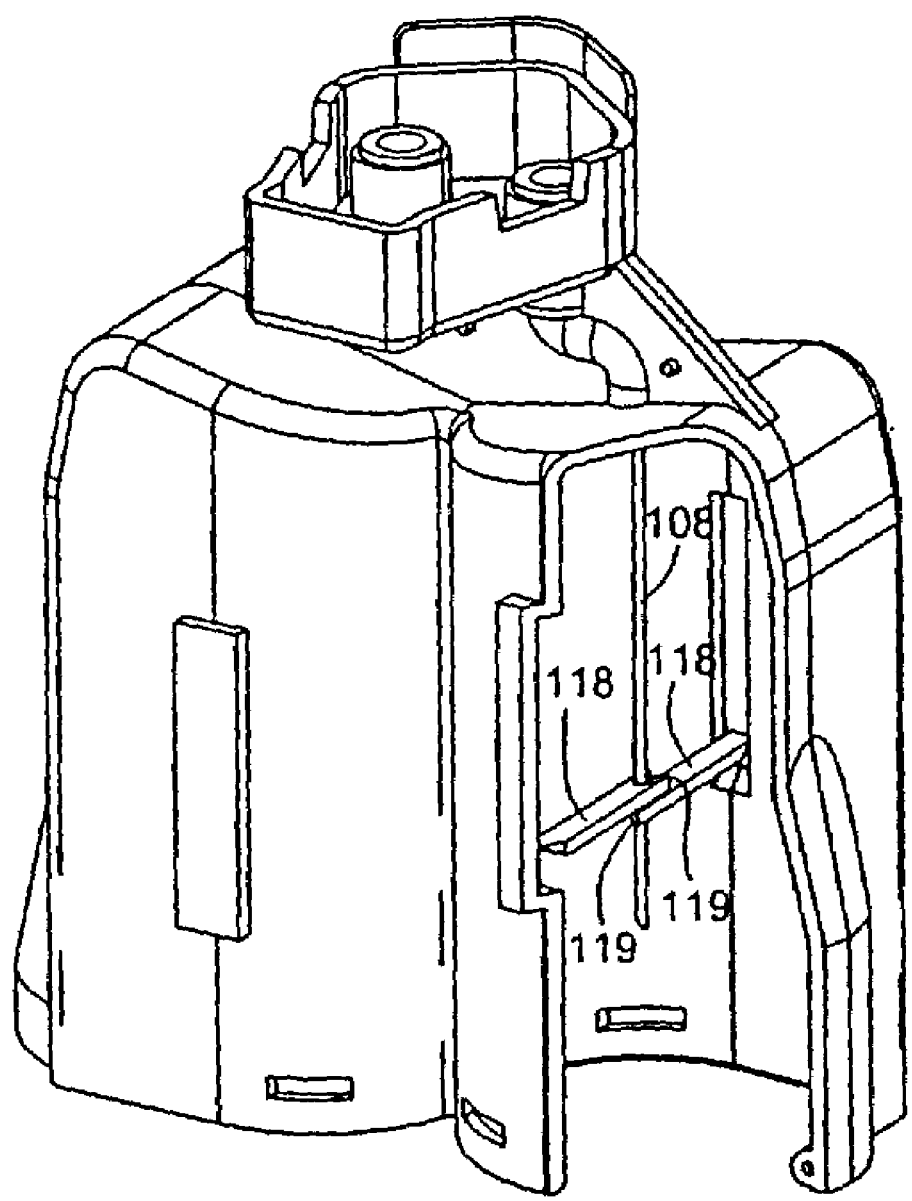
FIG. 13 is a cut away view showing the drawing tube held in place by the guide.

Drawing tube guides 118 and 120 are hinged within recesses 122 and 124 so that they may be housed within the recesses when the filling device used in use. FIG. 13 illustrates the manner in which drawing to 108 is held in place by drawing tube guides 118. Each of the guides has a forked end 119 which when used in conjunction with one another will hold drawing tube 118 in a vertical position. Recesses 122 and 124 should be of suitable size to allow for variations in the position of the guide, when it is being stored.

Collar 136 is connected to an applicator 18 by a pair of snap fit members 138. Applicator 18 is placed over direct dual filling device 100 such that the syringes of applicator 18 are approximately centered over inlet ports 140 and 142, then pressed down until in place by snap fit members 138. Alternatively, collar 136 may be configured without snap fit members 138. Due to the stability of the device when assembled, applicator 18 can be held in place by a combination of gravity and the friction generated by the tight nature of the seal formed between the syringes and the fluid conduits. The novel shaping of collar 136 allows direct dual filling device 100 to mate with applicator 18 in only one orientation, thereby "keying" the fill device to the applicator. The general pentagon shape precisely fits the applicator body in the same manner as interchangeable applicator tips or heads, which are used for droplet or spray dispensing of sealant. This feature of keying the filling device collar to the applicator insures the proper fibrin components are delivered to their respective reservoirs without significant risk of cross-contamination, and the resulting loss of materials caused by the cross-contamination.

Figure 8:
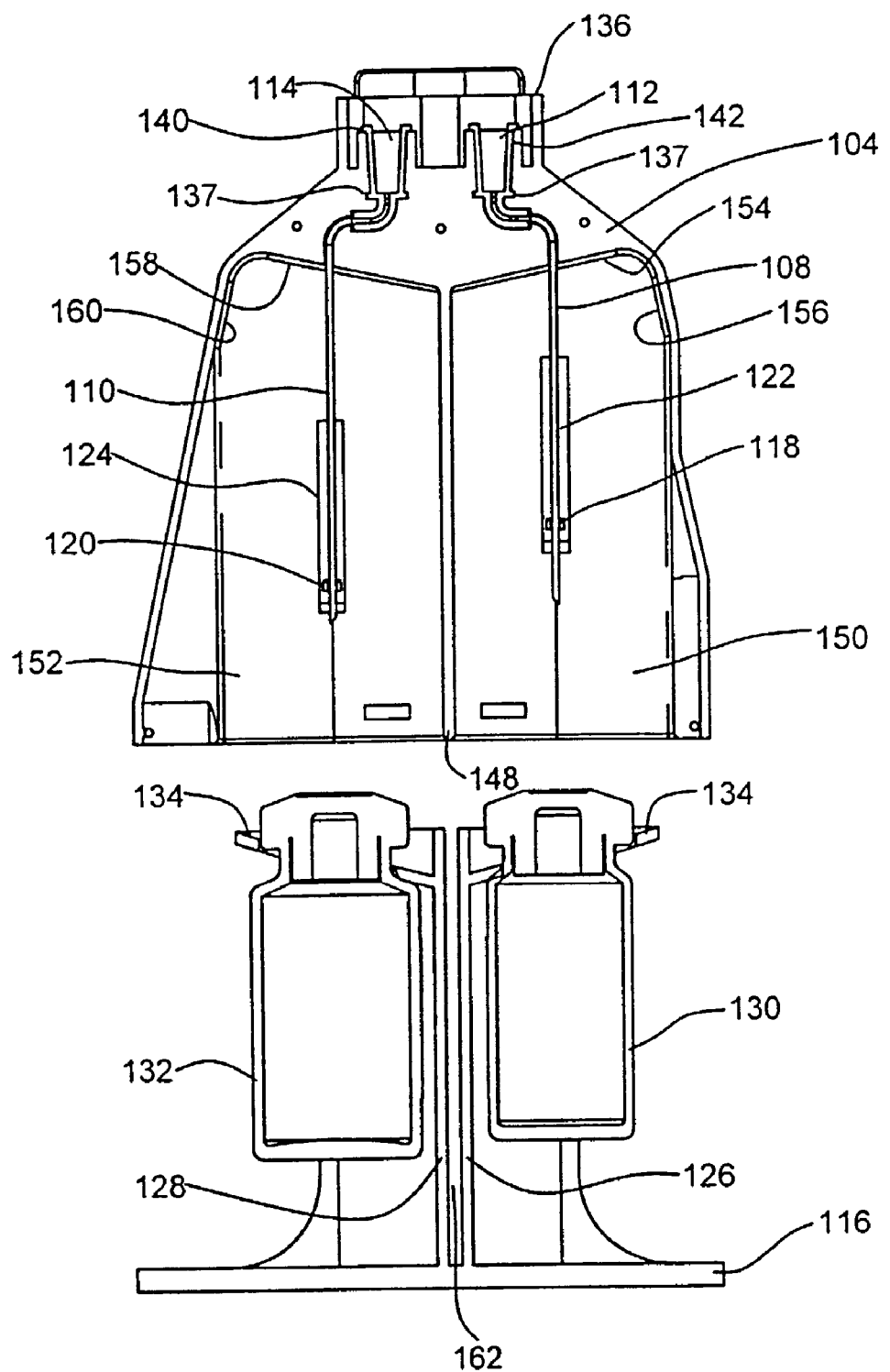
FIG. 8 is an elevational section view of an alternative embodiment of the present invention.

As shown in FIG. 8, first-half 104 of hood 102 has a central divider 148 which divides the hood into two compartments 150 and 152, which when hood 102 is assembled, house vials 130 and 132 respectively. Compartment 150 has an upper surface 154 which is slanted from its lowest point at divider 148 to its highest point at outer wall 156. Similarly, compartment 152 has an upper surface and 158 which is slanted from its lowest point at divider 148 to its highest point at outer wall 160.

Vial supports 126 and 128 are separated by divider slot 162 which is configured to receive central divider 148 of hood 102. Vial support surface 134 has a slanted outer portion 164, a level central portion 166, and an inner slanted U-shaped surface 168. The angle at which the inner and outer portions of vial support surface 134 is constructed, is substantially parallel to slanted upper surface 154 and 158 of hood 102. Vial support surface 134 has a width which allows vials 130 and 132 to be suspended by their necks as shown in FIG. 8.

The assembly of the components of filling device 100 can take place at a factory or other such manufacturing facility prior to use of the inventive device. Drawing tubes 108 and 110 are mated with tubular arms 146 of fluid conduits 112 and 114. The assembly is then snugly fitted within channel 137 such that drawing tubes 108 and 110 all are held by guides 118 and 120 respectively. Preferably, one half of channel 137 is of sufficient proportion to accommodate a greater portion of fluid conduits 112 and 114. This allows the fluid conduits to be placed within the larger channel prior to be two halves being assembled, thereby allowing for greater restraint of the conduits prior to assembling the two halves of hood 102.

Once the drawing tubes and fluid conduits are in place, first-half 104 and second-half 106, of hood 102 are configured to be assembled together by snap fit members 105. Alternatively, ultrasonic welding, glue, press fitting or any other method of assembly may be used. All of the components of the inventive device are then sterilized. When it is desired to use the inventive filling device the operator need only insert the vials and mate the hood onto the base.

Generally, the agent vials are not sterilized and are unable to be brought into a sterile environment without risk of contamination. However, when the agent vials are shrouded within the inventive filling device the assembly may be brought into a sterile environment for use.

The operator assembles the device by sliding the agent vials onto vial supports 126 and 128 such that the necks of the two agent vials are resting on vial support surface 134. The angle at which the outer portion 164 of vial support surface 134 is configured, will cause the two agent vials to slide down into place resting on level central portion 166 of vial support surface 134. The angle is such that friction will not stop the bottle from fully seating on level central portion 166. As shown and FIG. 10 a vial 130 is properly seated within vial support 126 when the center line 180 of vial 130 is positioned at a point on level central portion 166 further out than pivot fulcrum 182. Pivot fulcrum 182 occurs at the point where level portion 166 transforms into inner support surface 168. This positioning allows vial 130 to be firmly held in place by support 126, while still allowing vile 130 to pivot in the direction of arrow 184. By allowing vial 130 to fully seat within vial support surface 134, vial 130 will maintain a level position during the first part of the insertion of the drawing tube. This allows the needle to properly align with the target area of the vials septum. Since the vials septum has a thin portion in be center which allows needles to puncture, it is desirable to align the drawing tube with this target area, thereby assuring a good seal.

Figure 9:
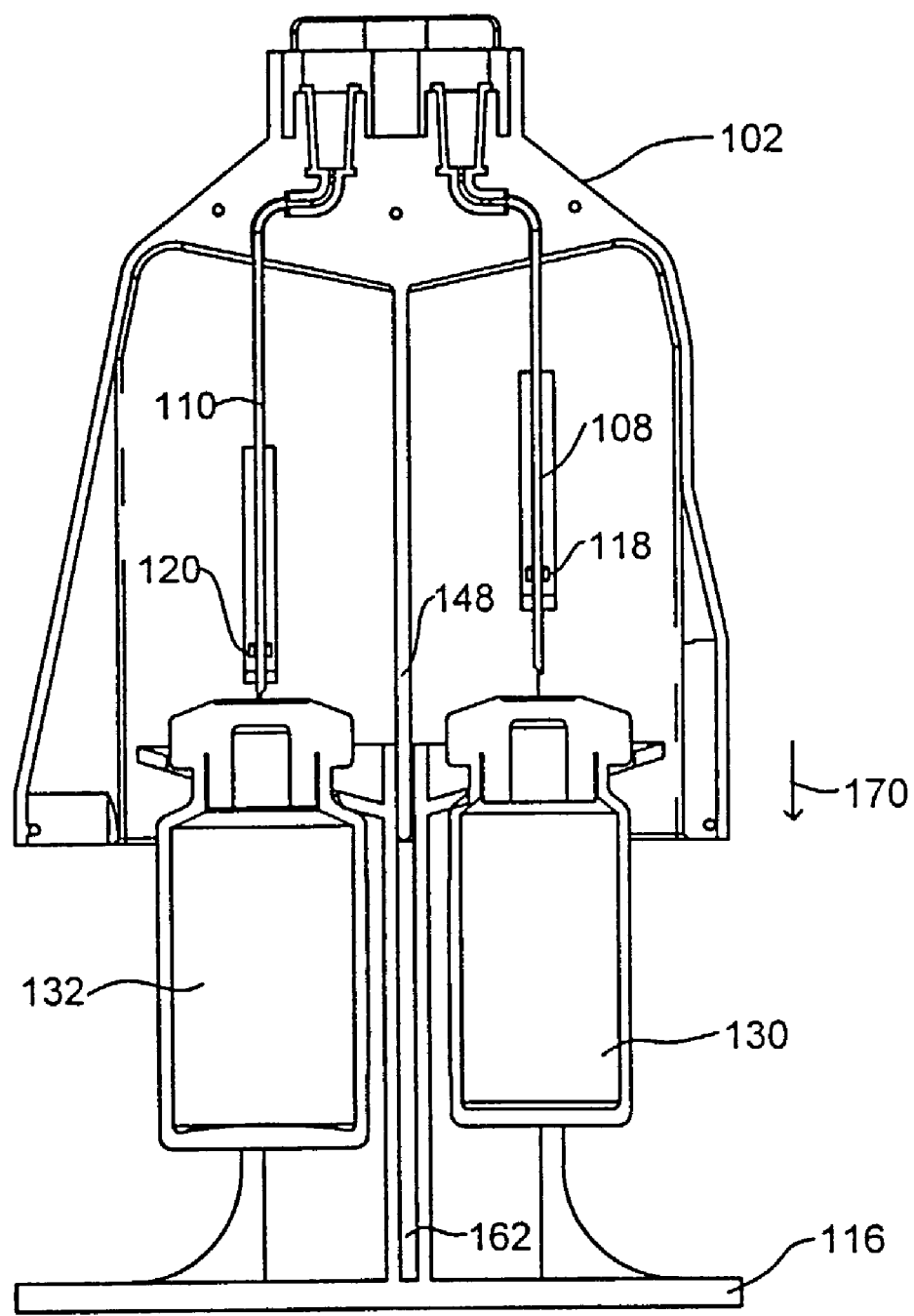
FIG. 9 is an elevational view of an alternative embodiment of the present invention.

Once the vials are properly seated, the hood assembly is placed over the base assembly such that divider 148 is positioned to engage within divider slot 162 as shown in FIG. 9. As the hood assembly is lowered onto the base in the direction of arrow 170, divider 148 and divider slot 162 act to align drawing tubes 108 and 110 with the target area of agent vials 130 and 132.

As the hood assembly is further lowered onto the base in the direction of arrow 170, drawing tubes 108 and 110 puncture the septa of the agent vials creating an airtight interface. As indicated earlier the drawing tubes should be held vertical by their guides and the agent vials positioned correctly by the vial support face so that the drawing tubes puncture the target area of the septa.

Figure 12:
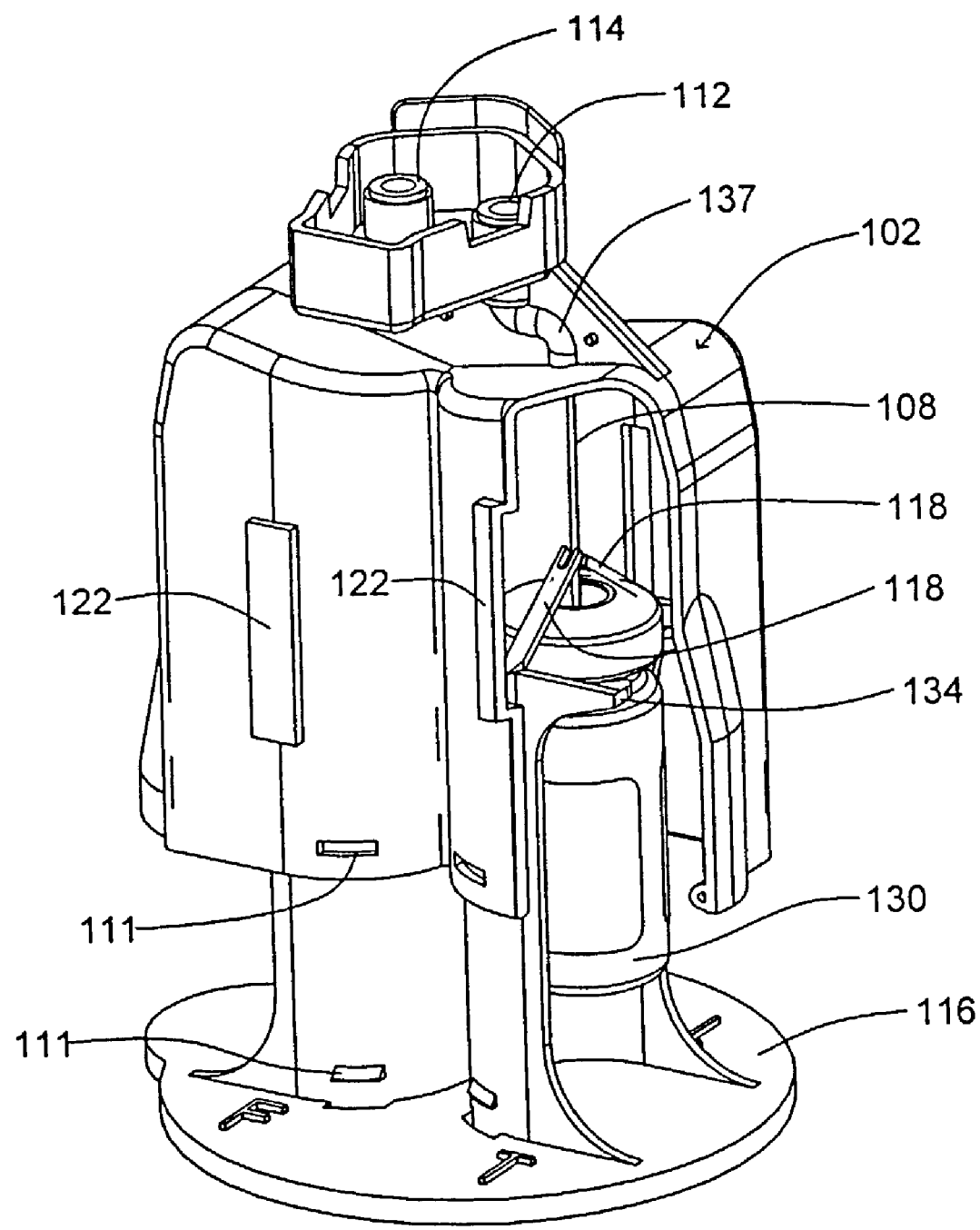
FIG. 12 is a cut away view showing the hood being lowered onto the base during assembly.

As illustrated in FIG. 12, when guides 118 and 120 come into contact with the top portion of agent vials 130 and 132 they all are folded up and out of the way into recesses 122 and 124.

Figure 10:
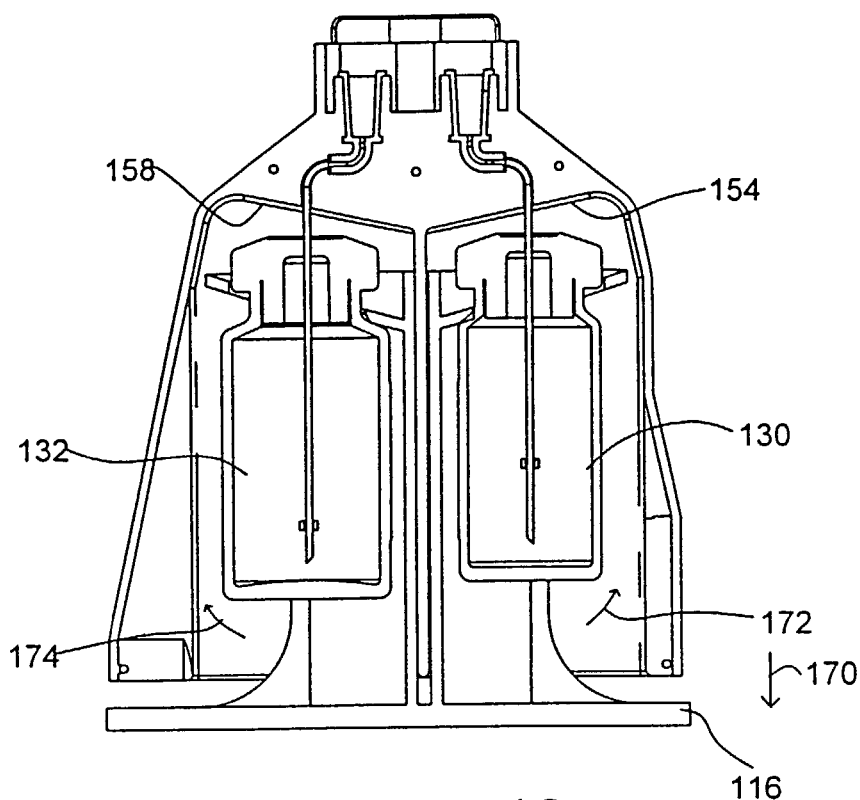
FIG. 10 is an elevational view of an alternative embodiment of the present invention.
Figure 10A:
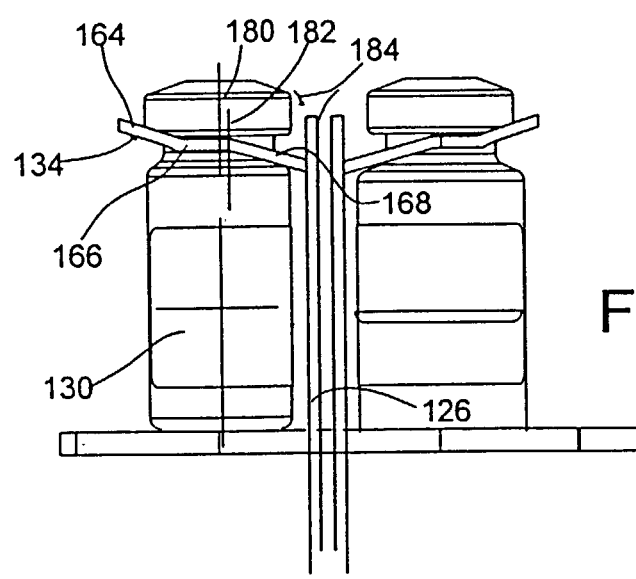
FIG. 10a is a partial elevational view depicting the vial support.

FIG. 10 depicts the point at which the top portion of vials 130 and 132 comes into contact with upper surfaces 154 and 158. As the housing moves onto the base in the direction of arrow 170, the slanted configuration of upper surface 154 causes agent vial 130 to tilt in the direction of arrow 172. Similarly, the slanted configuration of upper surface 158 causes agent vial 132 to tilt in the direction of arrow 174. The vials are tilted because the top slanted inner surface of the housing vial cavities are forced down onto the lid of each vial, causing them to tilt to the same angle as the top of the inner cavity.

Simultaneously with the tilting of agent viles 130 and 132, drawing tubes 108 and 110 are driven into the bottom corner of their respective viles. Ideally, the sharpened tips of the drawing tubes are shaped such that they conform to the shape of the bottom corner of the agent vials so that as much fluid as possible is drawn up.

Figure 11:
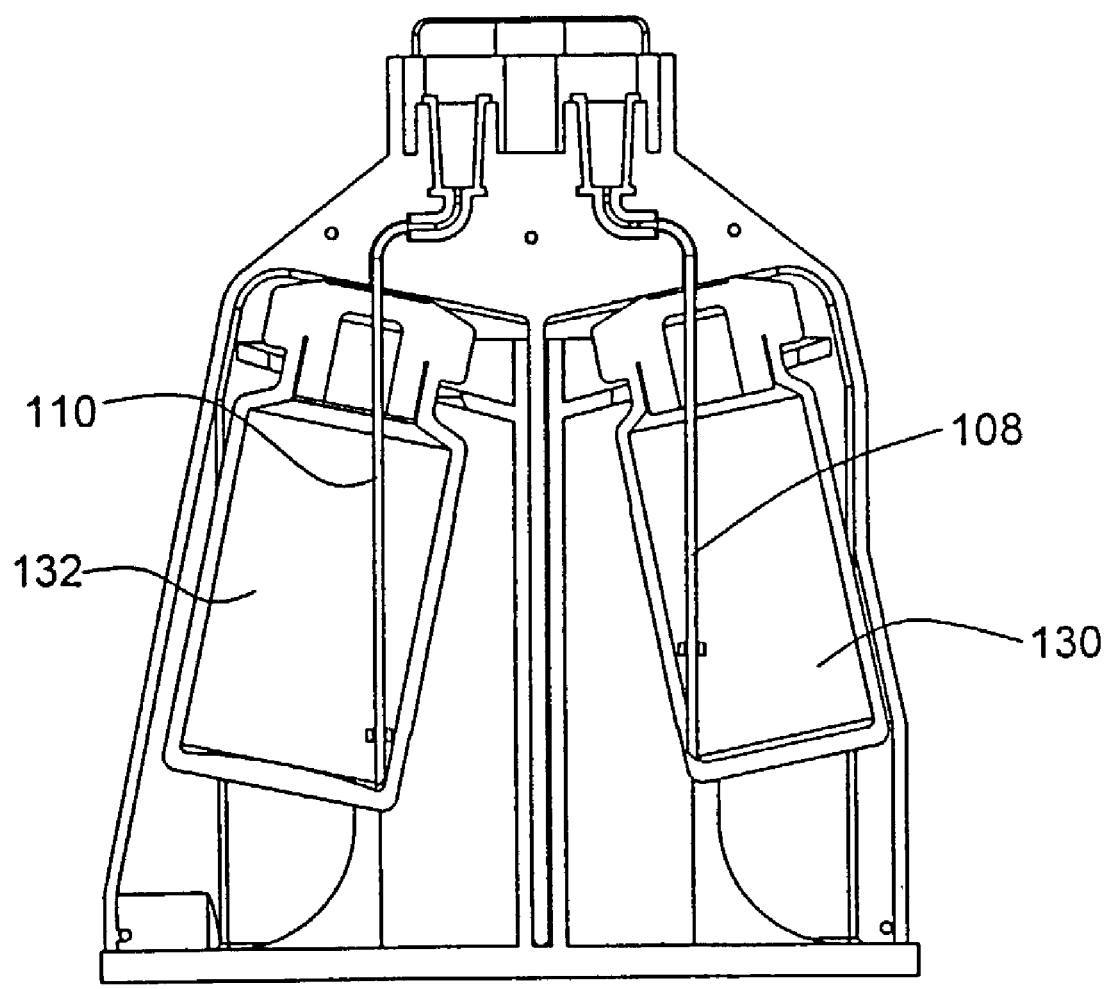
FIG. 11 is an elevational view of an alternative embodiment of the present invention.

Once the hood assembly has been completely lowered onto the base into the fully engaged position of FIG. 11, it may be locked into place by snap fittings 111. Agent vials 130 and 132 are tilted in such a manner that drawing tubes 108 and 110 are forced into the bottom corner of each respective vial, which has now become the low point for the agent to pool into. This configuration along with the shaping of the drawing tubes allows for minimal waste of the agent contained within the vials.

Once the inventive filing device is assembled, it may be brought into a sterile field. Although, the agent vials are generally not sterile and therefore would not be allowed within a sterile environment for risk of contamination, the hood and base assembly has effectively shrouded the vials within a sterile environment so that they may be brought into a sterile field.

Although only two bottles are depicted for use with the inventive filling device, adaptation can be easily made to allow the use of three or more, which can directly fill three or more reservoirs contained within the applicator. This adaptation can be accomplished by expanding the hood and adding another inlet port, transverse channel and drawing tube.

While illustrative embodiments of the invention have been described above, it is, of course, understood that various modifications will be apparent to those of ordinary skill in the art. Many such modifications are contemplated as being within the spirit and scope of the invention.

The invention claim is:

1. A connector for connecting a dispensing instrument to multiple containers, comprising:
    a) a body having a bottom and a top, said top having an outer perimeter and a plurality of outlet ports within said perimeter, said bottom having a plurality of inlet ports connected to said outlet ports wherein each of said inlet ports is connected to one of said outlet ports by a bore in said body;
    b) a collar extending from said perimeter, said collar being adapted to detachably receive said dispensing instrument;
    c) a plurality of tubes whereby each of said tubes is connected to one of said inlet ports and has an end distal to said inlet ports for extending into one of said containers, each of said ends having an opening for drawing fluid;

d) a hood extending from said bottom and adapted to simultaneously slidably receive a plurality of containers such that once the containers are seated within said hood, said ends of said tubes allow for simultaneous and separate drawing of fluids into said dispensing instrument wherein the dispensing instrument is capable of holding and dispensing fluid after being disengaged from the connector; and e) at least one tubular air vent attached to said connector wherein each air vent further comprises a first opening, a second opening, and a conduit connecting said first opening to said second opening and said first opening is positioned such that when said containers are locked to said hood, each of said first openings is situated inside each of said containers and each of said second openings is externally situated on said connector such that positive air pressure is supplied to each of said containers reducing any vacuum forces created within said containers during drawing.

2. A kit for drawing fluids from a plurality of containers comprising:

a) a plurality of containers wherein said containers are adapted to sealably hold fluids;

b) a dispensing instrument having at least two fluid reservoirs for separately holding and controllably dispensing fluids, said dispensing instrument further has a supply port connected to each fluid reservoir by a supply conduit;

c) a connector for coupling said dispensing instrument to said plurality of containers wherein said connector comprises:

i) a body having a bottom and a top, said top having an outer perimeter and a plurality of outlet ports within said perimeter, said bottom having a plurality of inlet ports connected to said outlet ports wherein each of said inlet ports is connected to one of said outlet ports by a bore in said body;

ii) a collar extending from said perimeter, said collar being adapted to detachably receive said dispensing instrument connecting said supply ports to said inlet ports of said connector;

iii) a plurality of tubes whereby each of said tubes is connected to one of said inlet ports and has an end distal to said inlet ports for extending into one of said containers, each of said ends having an opening from drawing fluid; and iv) a hood extending from said bottom and adapted to simultaneously slideably receive and releasably lock onto said plurality of containers such that once each of said plurality of containers is interlocked with said hood, said ends of said tubes allow for simultaneous and separated drawing of fluids into said fluid reservoirs of said dispensing instrument wherein the dispensing instrument is capable of holding and dispensing fluid after being disengaged from the connector, wherein said collar, said body, and said hood of said connector are formed as a single thermoplastic member.

3. A filling device to facilitate withdrawal into a syringe of a fluid from a container, the container having a top through which fluid can be passed into or out of the container and a bottom enabling the container to be supported upright on a flat surface, the filling device comprising:

a) a containerlocating member to position the container; and b) a syringe-locating member to align the syringe with the container for withdrawal of fluid from the container, wherein, in a filling mode, a fluid conduit extends from within the container to the syringe for passage of the fluid from the container to the syringe, and wherein, also in filling mode, the container-locating member orients the container in a tilted position to enhance removal of the fluid through the fluid conduit wherein the container has, in the tilted position, an inverted apex aligned with the fluid conduit to facilitate withdrawal of an optimal amount of fluid from the container;

wherein the syringe-locating member supports the syringe and is movable downwardly with the syringe toward the container and wherein the downward movement of the syringe-locating member tilts the container.

4. A filling device according to claim 3 wherein the downward movement of the syringe-locating member toward the container-locating member inserts the fluid conduit into the container.

5. A filling device according to claim 4 wherein the top of the fluid container is closed by a frangible seal, the fluid conduit has a downward tip structured to penetrate the frangible seal and wherein the downward movement of the syringe-locating member toward the container locating member penetrates the fluid conduit through the container frangible seal.

6. A filling device according to claim 3, further comprising c) a shroud to enclose the container and the fluid conduit in the filling mode.

7. A filling device according to claim 6 wherein the shroud provides a sealing enclosure permitting the filling device, when assembled with the syringe and the container, to be admitted to a sterile environment.

8. A filling device according to claim 4 wherein the top of the fluid container is closed by a frangible seal having its thinnest part in its center, the fluid conduit has a downward tip structured to penetrate the frangible seal and wherein the downward movement of the syringe-locating member toward the container-locating member penetrates the fluid conduit through the center of the container frangible seal.

9. A filling device to facilitate withdrawal of two fluids from two containers into a dual syringe fluid applicator having dual syringe reservoirs, each container having a top through which fluid can be passed into or out of the container and a bottom enabling the container to be supported upright on a flat surface, the filling device comprising:

a) a container-locating member to position each container; and b) a syringe-locating member to align each syringe with the respective container for withdrawal of fluid from the respective container, wherein, in a filling mode, a fluid conduit extends from within each container to the respective syringe for passage of the fluid from each container to each syringe, and wherein, also in the filling mode, the container-locating member orients each container in a tilted position to enhance removal of the fluid through the respective fluid conduit wherein each container has, in the tilted position, an inverted apex aligned with the respective fluid conduit to facilitate withdrawal of an optimal amount of fluid from the respective container;

wherein the syringe-locating member locates the dual syringes in side-byside relationship, the two fluid conduits are provided for separately conveying fluids from the two containers to the dual syringe reservoirs, the container-locating member provides for side-by-side location of the two fluid containers in alignment with the fluid conduits and wherein, in the filling mode, both containers are tilted to enhance removal of the fluids from the container.

10. A method of separately transferring two fluids stored in two containers into a dual-syringe fluid applicator, comprising:

a) locating the containers in side-by-side relationship in a filling device;

b) simultaneously titling the containers to align a lower most point of each container with separate withdrawal syringes of the filling device;

c) connecting each fluid reservoir of the dual-syringe fluid applicator with separate fluid conduits in communication with the separate withdrawal syringes of the filling device; and d) operating the applicator to draw the fluids simultaneously and separately from the containers through the fluid conduits into each fluid reservoir in the dual syringe fluid applicator.

11. A method according to claim 10 further comprising moving the dual syringe fluid applicator and the fluid conduits downwardly to insert the fluid conduits into the containers, prior to drawing the fluid into the fluid applicator.

* * * * *